(12) United States Patent
Toriumi (10) Patent No.: US 7,846,741 B2
(45) Date of Patent: *Dec. 7, 2010

(54) METHOD OF MANUFACTURING AN ANALYTICAL SAMPLE AND METHOD OF ANALYZING AN ANALYTICAL SAMPLE

(75) Inventor: Satoshi Toriumi, Ebina (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/726,367

(22) Filed: Mar. 18, 2010

(65) Prior Publication Data

US 2010/0171034 A1  Jul. 8, 2010

Related U.S. Application Data

(63) Continuation of application No. 11/976,375, filed on Oct. 24, 2007, now Pat. No. 7,727,773.

(30) Foreign Application Priority Data

Oct. 31, 2006   (JP) ............................. 2006-296745

(51) Int. Cl.
*G01N 24/00* (2006.01)
(52) U.S. Cl. ..................... 436/173; 528/15; 528/30; 528/31; 528/32; 528/33; 528/34; 528/36; 528/42; 526/279; 556/413; 556/450; 556/457; 556/458; 556/459
(58) Field of Classification Search ............ None
See application file for complete search history.

(56) References Cited

U.S. PATENT DOCUMENTS

| 2,814,601 A | 11/1957 | Currie et al. |
| 6,218,499 B1 | 4/2001 | Tarumi et al. |

(Continued)

FOREIGN PATENT DOCUMENTS

JP   9-210885   8/1997

(Continued)

OTHER PUBLICATIONS

Yeo et al., SIMS backside depth profiling of ultrashallow implants using silicon-on-insulator substrates, 2002, Surface and Interface Analysis, vol. 33, pp. 373-375.

*Primary Examiner*—Yelena G Gakh
*Assistant Examiner*—Robert Xu
(74) *Attorney, Agent, or Firm*—Eric J. Robinson; Robinson Intellectual Property Law Office, P.C.

(57) ABSTRACT

A method of manufacturing an analytical sample by a secondary ion mass spectrometry method is provided, which comprises a step of forming a separation layer over a substrate, a step of forming one of a thin film and a thin-film stack body to be analyzed over the separation layer, a step of forming an opening portion in one of the thin film and the thin-film stack body, a step of attaching a supporting body to one of a surface of the thin film and a surface of a top layer of the thin-film stack body, and a step of separating one of the thin film and the thin-film stack body from the substrate.

15 Claims, 12 Drawing Sheets

U.S. PATENT DOCUMENTS

| | | |
|---|---|---|
| 6,875,674 B2 | 4/2005 | Asami et al. |
| 7,351,300 B2 | 4/2008 | Takayama et al. |
| 7,465,966 B2 | 12/2008 | Ichijo et al. |
| 7,521,383 B2 | 4/2009 | Morisue et al. |
| 2006/0270195 A1 | 11/2006 | Yamada et al. |

FOREIGN PATENT DOCUMENTS

| | | |
|---|---|---|
| JP | 11-326164 | 11/1999 |
| JP | 2000-105180 | 4/2000 |
| JP | 2000-121520 | 4/2000 |
| WO | WO 2006/123825 | 11/2006 |

# METHOD OF MANUFACTURING AN ANALYTICAL SAMPLE AND METHOD OF ANALYZING AN ANALYTICAL SAMPLE

BACKGROUND OF THE INVENTION

1. Field of the Invention

The present invention is related to a method of manufacturing an analytical sample. In specific, the present invention is related to a method of manufacturing a SIMS sample.

2. Description of the Related Art

In production of industrial products, such as semiconductor devices, it is important to see concentration distribution of elements in the depth direction. For example, in a semiconductor element mounted over a semiconductor device, such as a field effect transistor (hereinafter referred to as a FET) or a thin film transistor (hereinafter referred to as a TFT), which is a kind of an FET; whether conditions of impurity introduction is suitable or not can be studied according to the concentration distribution of impurities in an impurity region in a semiconductor layer.

As a typical analysis method to reveal concentration distribution in the depth direction, secondary ion mass spectroscopy (hereinafter referred to as SIMS), auger electron spectroscopy (hereinafter referred to as AES), and X-ray photoelectron spectroscopy (hereinafter referred to as XPS) can be given. These analysis methods differ from one another in detection sensitivity, element discrimination capability, and the like; therefore, they are selected in accordance with the purpose. SIMS is an analysis method which is especially excellent in detection sensitivity and element discrimination capability.

In SIMS, a solid sample to be analyzed is irradiated with primary ions so that a surface of the solid sample is sputtered, and thus, ionized molecules or atoms are emitted from the solid sample surface and these ionized secondary ions are detected with a mass spectrometer. When a SIMS method is used, the concentration of impurity elements in a solid sample in which a thin film is formed on one main surface of a substrate and impurity elements are added to the thin film by ion implantation or the like, such as a TFT formed over an insulating substrate, can be analyzed. However, in analyzing such a solid sample, when the solid sample is irradiated with primary ions from a surface side of a thin film, the thin film is sputtered by primary ions, so that a crater is formed and the shape of the surface changes with time. Secondary ions are detected from side surfaces of a crater by a shape effect generated due to change in surface shape with time (crater edge effect); accordingly, accuracy of data in the depth direction decreases. Therefore, it is preferable to irradiate a rear surface (where a thin film is not formed) of a solid sample with primary ions instead of a front surface (where the thin film is formed) of the solid sample in order to precisely analyze the dose of impurity elements for imparting one conductivity in the thin film of the solid sample. To analyze a sample in such a manner, a following method may be employed: a surface of the top layer of an analytical sample is fixed to a table for polishing and a substrate is processed by polishing from a rear surface side by chemical mechanical polishing (hereinafter referred to as CMP) and the like to be as thin as about 1 µm, then the rear surface side of the substrate is irradiated with primary ions so as to be analyzed by SIMS.

SIMS analysis usually needs a structure which is not affected by charge build-up. Therefore, a material which is not electrically charged (e.g., silicon wafer) is necessarily laid under a film to be analyzed so that the film to be analyzed is not at a floating potential. Further, even in the case of using an insulating substrate, such as a glass substrate, if excessive charge build-up does not occur, the use of a neutralization gun provided for electrical neutralization (e.g., electron gun) allows a sample to be analyzed.

A polishing apparatus, such as a CMP apparatus is used for polishing the rear surface of the substrate. A CMP apparatus is provided with a polishing pad, a holding head (a head for fixing a sample), and a slurry (which contains a powder for mechanical polishing). As conditions for polishing, there are a load (force applied vertically to a polishing surface (a contact surface between the polishing pad and the holding head)), rotating speed, and the kind of the slurry, and these conditions are not easily determined. For example, it is difficult to polish the substrate to be as thin as about 1 µm while keeping the sample flat, which may need skills along with a wealth of experiences. In addition, the amount of polishing per unit time is reduced and polishing is conducted carefully, the time required is increased.

As described above, a method in which a rear surface of a substrate is polished and the polished surface is irradiated with primary ions for analysis by SIMS are troublesome for processing by polishing, and needs a great deal of time for pretreatment when many samples are evaluated. Further, advanced skill is needed for processing by polishing. Furthermore, flatness of the substrate may be lost due to the polishing step described above, which brings problems in precision in analysis by SIMS (e.g., see Patent Document 1: Japanese Published Patent Application No. H9-210885).

SUMMARY OF THE INVENTION

As described above, in a method in which a rear surface of a substrate is polished and the polished surface is irradiated with primary ions for analysis by SIMS, the substrate is polished with a CMP technique or the like; accordingly, a large amount of time is consumed to process an analytical sample. In addition, advanced skill is needed to determine conditions of polishing to polish the analytical sample with uniformity and flatness thereof being kept. Thus, although a method in which a rear surface of a substrate is polished and the polished surface is irradiated with primary ions for analysis by SIMS enables more precise analysis than conventional SIMS in which a front surface is irradiated with primary ions, there is a problem in that an analytical sample is not easily manufactured.

In accordance with the foregoing, it is an object of the present invention to provide a method of manufacturing an analytical sample, and a method of SIMS which can be easily and more precisely carried out as compared with a conventional method.

One mode of the present invention is a method of manufacturing an analytical sample, which includes forming a thin film or a thin-film stack body to be analyzed over a substrate, attaching a supporting body to the outermost surface of the thin film or the outermost surface of the top layer of the thin-film stack body, and separating the thin film or the thin-film stack body from the substrate.

Another mode of the present invention is a method of manufacturing an analytical sample, which includes forming a separation layer over a substrate, forming a thin film or a thin-film stack body to be analyzed over the separation layer, attaching a supporting body to the outermost surface of the thin film or the outermost surface of the top layer of the thin-film stack body, and separating the thin film or the thin-film stack body from the separation layer.

Another mode of the present invention is a method of manufacturing an analytical sample to be analyzed by a secondary ion mass spectrometry method, which includes forming a separation layer over a substrate, forming a thin film or a thin-film stack body to be analyzed over the separation layer, attaching a supporting body to the outermost surface of the thin film or the outermost surface of the top layer of the thin-film stack body, and separating the thin film or the thin-film stack body from the separation layer.

The method of manufacturing an analytical sample which is described above may further include forming a relief layer between the separation layer and the thin film or the thin-film stack body which is to be analyzed.

In the present invention described above, a film with a higher fluorine concentration than the relief layer is preferably used as the separation layer.

In the present invention described above each of the separation layer and the relief layer is preferably a film with a fluorine concentration of $1\times10^{17}$ atoms/cm$^3$ or more and $2\times10^{19}$ atoms/cm$^3$ or less, a hydrogen concentration of $1\times10^{21}$ atoms/cm$^3$ or more and $1\times10^{22}$ atoms/cm$^3$ or less, a carbon concentration of $1\times10^{15}$ atoms/cm$^3$ or more and $2\times10^{18}$ atoms/cm$^3$ or less, a nitrogen concentration of $1\times10^{18}$ atoms/cm$^3$ or more and $1\times10^{20}$ atoms/cm$^3$ or less, and an oxygen concentration of $1\times10^{15}$ atoms/cm$^3$ or more and $1\times10^{19}$ atoms/cm$^3$ or less is preferably formed.

In the present invention having any of the foregoing structures, the supporting body preferably has a base material and an adhesive provided on one main surface of the base material, and the adhesive is preferably formed of a silicone-based adhesive.

In the present invention having any of the foregoing structures, an amorphous silicon film containing fluorine is preferably formed as the separation layer.

Note that a silicone-based adhesive is an adhesive which contains organopolysiloxane as its main component. Since silicone includes a Si—O bond, it is similar to an inorganic high molecular compound; however, silicone behaves like an organic high molecular compound due to an organic group bonded to Si (e.g., a methyl group or a phenyl group).

According to the present invention, concentration distribution in the depth direction in a target analyte can be analyzed highly precisely without a complicated technique.

According to the present invention, a polishing step like CMP is not necessarily carried out, which is needed in a SIMS method in which a rear surface of a substrate is polished and the polished surface is irradiated with primary ions for analysis. Therefore, the time, cost, and the like which are consumed by polishing in a method in which a rear surface of a substrate is polished and the polished surface is irradiated with primary ions for analysis by SIMS can be saved. Since time is not consumed by polishing, concentration distribution in the depth direction can be analyzed in a short time as compared with a conventional method.

DETAILED DESCRIPTION OF THE INVENTION

Embodiment Mode

Hereinafter, an embodiment mode and embodiments of the present invention are described with reference to the drawings. The present invention can be carried out in many different modes, and it is easily understood by those skilled in the art that modes and details can be modified in various ways without departing from the purpose and the scope of the present invention. Accordingly, the present invention should not be interpreted as being limited to the description of the embodiment mode.

Figure 1:
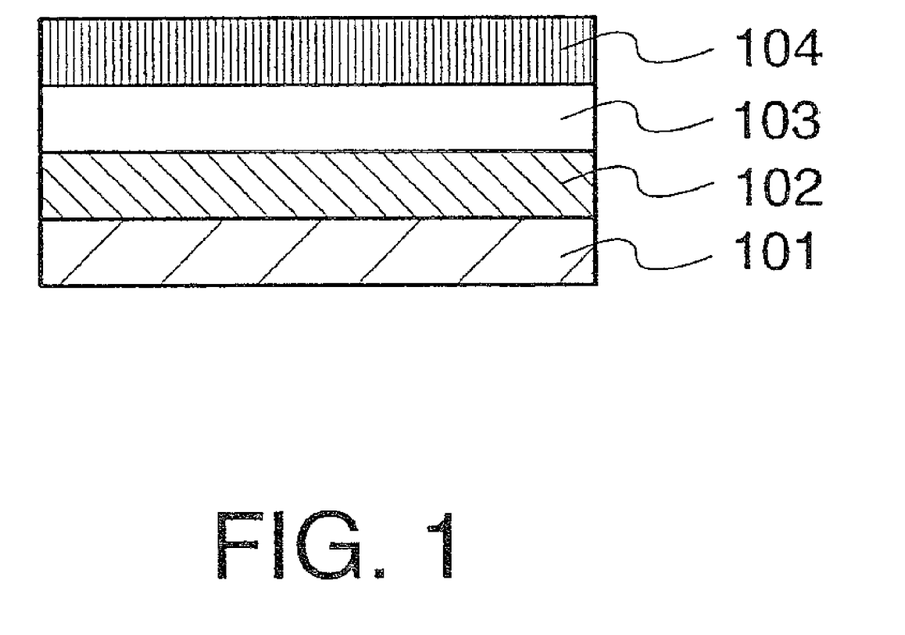
FIG. 1 is a schematic diagram of an analytical sample manufactured according to the present invention.

FIG. 1 is a cross-sectional view schematically showing a mode of an analytical sample manufactured according to the present invention. The analytical sample of FIG. 1 includes a supporting body 101, a thin-film stack body 102, a relief layer 103, and a separation layer 104.

Then, a method of manufacturing the analytical sample shown in FIG. 1 is described with reference to FIGS. 2A to 2D.

Figure 2A:
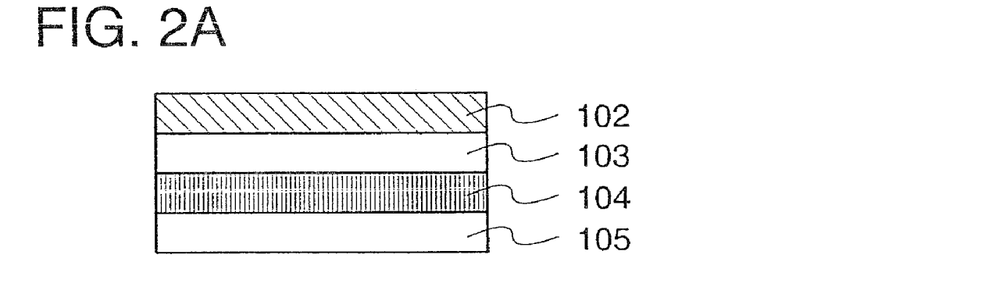
FIGS. 2A to 2D are diagrams illustrating a manufacturing process of an analytical sample according to the present invention.

First, the separation layer 104, the relief layer 103, and the thin-film stack body 102 are sequentially formed to be stacked over the substrate 105 (see FIG. 2A).

As the substrate 105, a mirror-polished silicon wafer, a glass substrate, or the like is used. For a glass substrate, quartz glass, low-melting point glass, or the like may be used. Note that the maximum temperature which low-melting point glass can withstand is about 700° C. When a glass substrate is used as the substrate 105, a film deposited over a large glass substrate, which may be used for a flat panel display typified by a liquid crystal display device, an EL display device, or the like, can be evaluated.

The separation layer 104 is not particularly limited as long as the separation layer does not become a contaminant source in an analysis apparatus. The separation layer 104 can be formed using, for example, a semiconductor material like silicon (Si), or a conductive material, such as tungsten (W), molybdenum (Mo), titanium (Ti), or tantalum (Ta). A silicon film is preferably used as the separation layer 104. More preferably, a silicon film containing fluorine (F) is used. When the separation layer 104 is formed using a silicon film containing fluorine, separation becomes easy. As such a silicon film containing fluorine, in specific, a silicon film which contains $1.0\times10^{17}$ atoms/cm$^3$ or more and $2.0\times10^{19}$ atoms/cm$^3$ or less of fluorine (F) is preferably used. More preferably, a silicon film containing $1.0\times10^{17}$ atoms/cm$^3$ or more and $2.0\times10^{19}$ atoms/cm$^3$ or less, hydrogen (H) at $1.0\times10^{21}$ atoms/cm$^3$ or more and $1.0\times10^{22}$ atoms/cm$^3$ or less of fluorine (F), $1.0\times10^{15}$ atoms/cm$^3$ or more and $2.0\times10^{18}$ atoms/cm$^3$ or less of carbon (C), $1.0\times10^{18}$ atoms/cm$^3$ or more and $1.0\times10^{20}$ atoms/cm$^3$ or less of nitrogen (N), and $1.0\times10^{15}$ atoms/cm$^3$ or more and $1.0\times10^{19}$ atoms/cm$^3$ or less of oxygen is preferably used. When concentrations are set in the foregoing ranges, separation becomes easy. Note that, when a film containing a metal element or an organic substance is used as the separation layer 104, a material which does not or hardly contaminate the insides of an analysis apparatus and a CVD apparatus is used.

The relief layer 103 is formed in order to relieve physical force in separation of the thin-film stack body 102 which is formed over the separation layer 104. Conditions for forming the relief layer 103 and the separation layer 104 can be the same or different. In addition, the relief layer 103 may have a film quality and a film thickness for relieving the physical force in the separation of the thin-film stack body 102. When a silicon film with a lower fluorine concentration than the separation layer 104 is formed as the relief layer 103, the separation layer is separated from the substrate, which is preferable. In addition, the relief layer can relieve physical force effectively, which is preferable.

Figure 3:
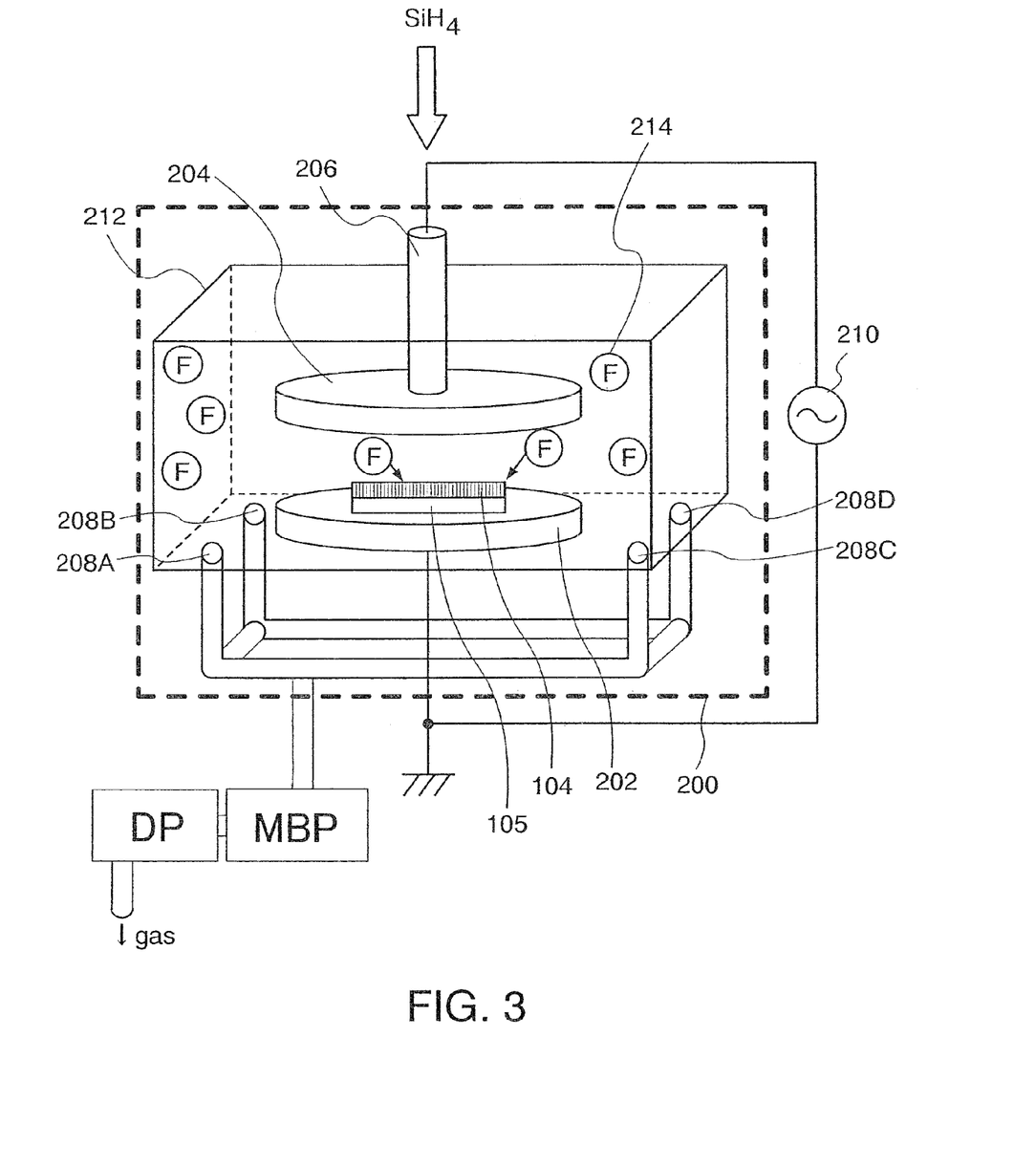
FIG. 3 is a schematic diagram of a capacitively coupled plasma CVD apparatus for forming a silicon film according to the present invention.

Here, a method of manufacturing the separation layer 104 and the relief layer 103 using a plasma CVD method is described. FIG. 3 shows one structural example of a capacitively coupled plasma CVD apparatus. The capacitively coupled plasma CVD apparatus 200 shown in FIG. 3 has a process chamber 212 including a substrate electrode plate 202, a high-frequency electrode plate 204, a gas introducing portion 206, and an exhaust port 208. Note that FIG. 3 shows a mode of the capacitively coupled plasma CVD apparatus 200 having four exhaust ports, but the present invention is not limited thereto. Note that exhaust ports 208A, 208B, 208C, and 208D are collectively referred to as the exhaust port 208. The exhaust port 208 is connected to a vacuum pump. Here, the exhaust port 208 is connected to a mechanical booster pump (MBP in FIG. 3), the mechanical booster pump is connected to a dry pump (DP in FIG. 3), and gas is exhausted though the dry pump. The substrate electrode plate 202 and the high-frequency electrode plate 204 are arranged in parallel. The substrate electrode plate 202 and the high-frequency electrode plate 204 are connected to an AC power source 210, and the substrate electrode plate 202 is at a ground potential. Note that an impedance of the capacitively coupled plasma CVD apparatus 200 is adjusted by a matching box. An object to be treated (the substrate 105 in FIG. 3) is held by the substrate electrode plate 202. The electric discharge of the capacitively coupled plasma CVD apparatus 200 is carried out by the AC power source 210 and plasma is generated between the substrate electrode plate 202 and the high-frequency electrode plate 204.

Cleaning is carried out with a fluorine-based gas in a process chamber of the plasma CVD apparatus as shown in FIG. 3. For example, a nitrogen trifluoride (NF$_3$) gas with a flow rate of 100 SCCM and an argon (Ar) gas with a flow rate of 50 SCCM are introduced through the gas introducing portion 206 into the process chamber 212 and etching may be carried out under a pressure of 13 Pa, a substrate temperature of 300° C., and a 27-MHz RF oscillator output of 300 W. After the cleaning in the process chamber 212, a separation layer of a silicon film with a high fluorine concentration is formed by an autodoping method utilizing fluorine 214 remaining in the process chamber 212 and successively, a silicon film is deposited. Thus, the relief layer 103 of a silicon film with a low fluorine concentration can be formed over the separation layer 104. For example, a monosilane (SiH$_4$) gas with a flow rate of 100 SCCM is introduced through the gas introducing portion 206 into the process chamber 212 and a silicon film is formed to have a thickness about 500 nm under a pressure of 33 Pa, a substrate temperature of 300° C., and a 27-MHz RF oscillator output of 170 W. The silicon film thus formed has a high fluorine concentration in its lower layer, which is on the substrate side, and a low fluorine concentration in its upper layer, accordingly, the lower layer part of the silicon film with a high fluorine concentration serves as a separation layer and the upper layer part of the silicon film with a low fluorine concentration serves as a relief layer. The formed silicon film includes the separation layer having a thickness of about 50 nm and the relief layer having a thickness of about 500 nm.

The thin-film stack body 102 may be foliated using appropriate single or stacked thin films to be analyzed. For example, a semiconductor film containing silicon or an inorganic semiconductor film, such as an oxide film or a nitride film containing silicon oxide, silicon nitride, silicon oxynitride, silicon nitride oxide, or the like is used. Note that in this specification, when the thin film to be analyzed has a single layer structure, the thin film is referred to as a thin-film stack body for convenience.

Note that in this specification, silicon oxynitride refers to a substance of which larger composition ratio of oxygen is higher than nitrogen, which can be also referred to as silicon oxide containing nitrogen. Similarly, silicon nitride oxide refers to a substance of which larger composition ratio of nitrogen than oxygen, which can be also referred to as silicon nitride containing oxygen.

Figure 4A:
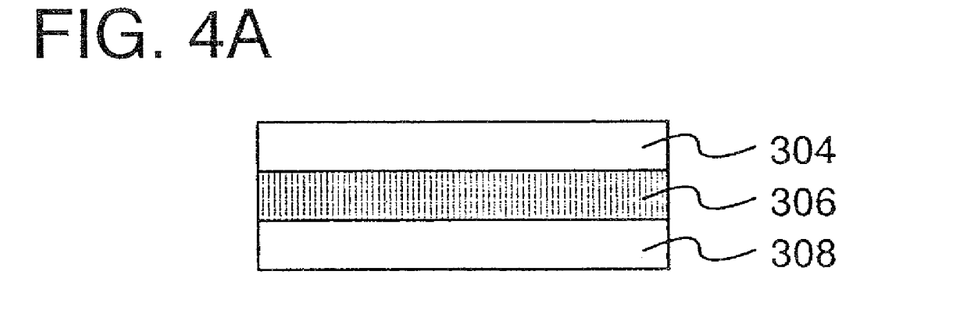
FIGS. 4A to 4C are schematic diagrams of an analytical sample manufactured according to the present invention.
Figure 4B:
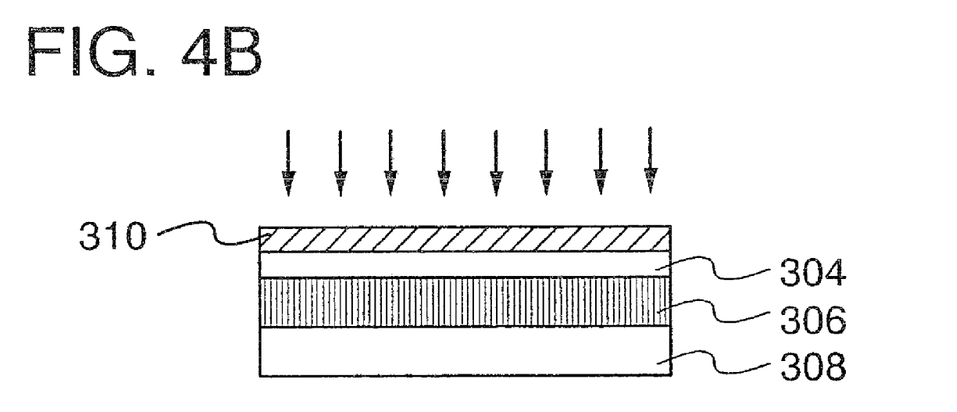
Figure 4C:
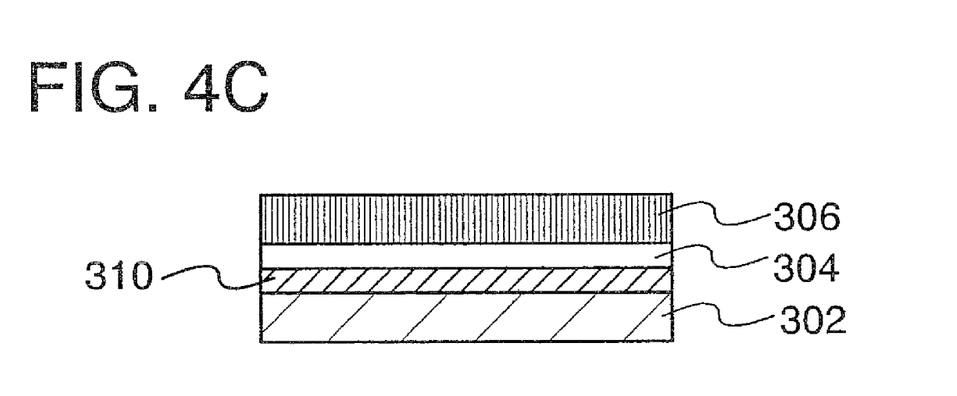

As shown in FIGS. 4A to 4C, a lower layer of a film to be analyzed may also serve as a relief layer. An analytical sample shown in FIG. 4A has a separation layer 306 formed over a substrate 308 and a film 304 to be analyzed over the separation layer 306. A lower layer of the film 304 to be analyzed may serve as a relief layer. For example, a silicon film is formed as the film 304 to be analyzed, a region 310 doped with an impurity element by doping is formed in the film 304 to be analyzed (see FIG. 4B), and a supporting body 302 having an adhesive property is attached so that separation is carried out (see FIG. 4C). Thus, the depth which the impurity element reaches in the silicon film when the silicon film is doped with the impurity element can be detected. Further, according to the present invention, information about the substrate which is detected in a method in which a rear surface of a substrate is polished and the polished surface is irradiated with primary ions for SIMS analysis is not detected, so that a crater edge effect can be reduced; accordingly the dose and the like of the impurity element can be evaluated with excellent accuracy.

Figure 2B:
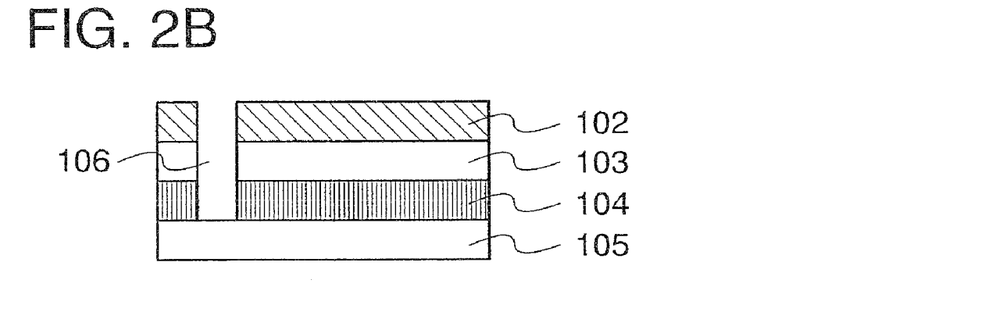

Then, an opening portion 106 is formed in the separation layer 104, the relief layer 103, and the thin-film stack body 102 which are stacked over the substrate 105 (see FIG. 2B).

Note that the opening portion 106 may be formed by, for example, making a cut using a physical means (e.g., laser, a sharp item like a cutter). When the opening portion 106 is formed in the separation layer 104, the relief layer 103, and the thin-film stack body 102; the thin-film stack body 102, which is to be an analytical sample can be easily peeled off from the substrate.

Then, an adhesive surface of the supporting body 101 is attached to a surface of the top layer of the thin-film stack body 102. The supporting body 101 is attached to cover the opening portion 106 partially or entirely (see FIG. 2C).

Figure 2C:
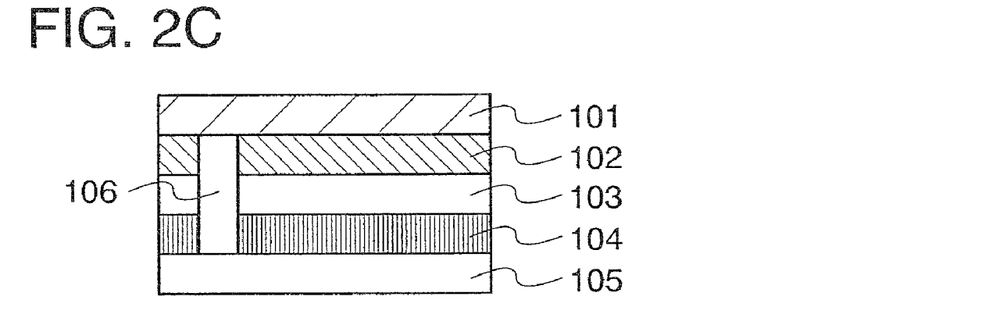

The supporting body 101 uses a material with high thermal resistance which does not contaminate the inside of the SIMS apparatus, which is kept in high vacuum or ultra-high vacuum, to an extent that an analytical result is affected by contamination. In analysis by SIMS, in order to prevent electrification (charge build-up) due to irradiation with primary ions to the analytical sample in analysis, a neutralization gun (e.g., an electron gun emitting electrons) which emits charge with opposite polarity with respect to charge of the electrification may be used and emit charge. At this time, the temperature of the analytical sample may rise by being heated due to irradiation by a neutralization gun; accordingly, the thermal resistance of the supporting body 101 refers to thermal resistance which makes the supporting body 101 withstand that rise in temperature. In addition, since the analytical sample may be heated due to irradiation by the neutralization gun or the like in analysis as described above, the supporting body 101 having one surface provided with an adhesive of which contamination does not affect the analytical result is necessarily selected in consideration of the rise in temperature due to the heating. In the supporting body 101, polyimide, a Kapton (registered trademark) film, or the like can be used as a base material and a silicone-based adhesive can be used as the adhesive. A Kapton (registered trademark) tape is preferably used as the supporting body 101.

Figure 5A:
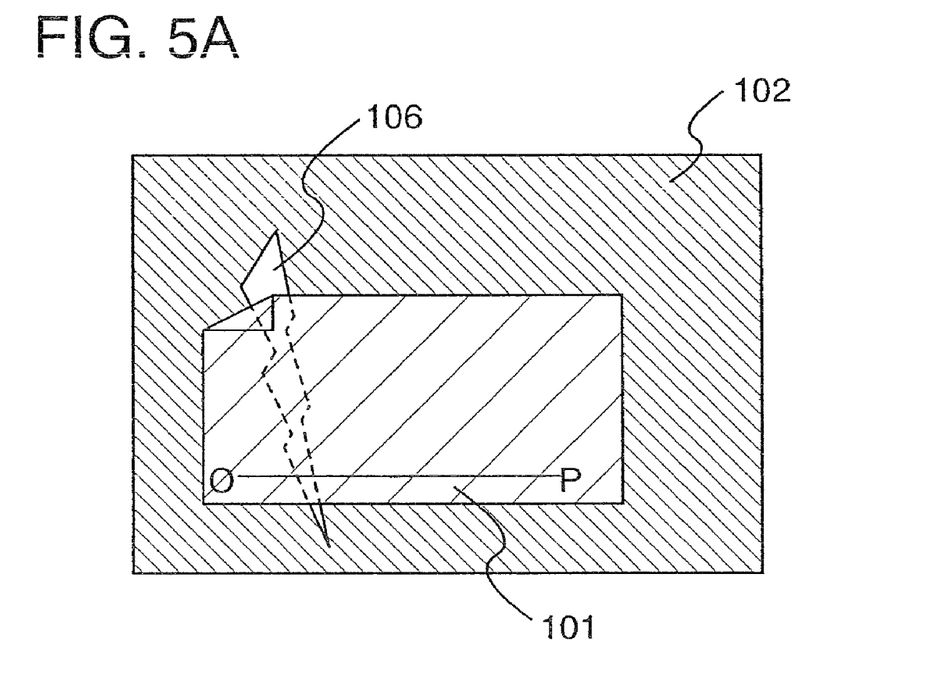
FIGS. 5A and 5B are diagrams illustrating manufacturing steps of an analytical sample according to the present invention.
Figure 5B:
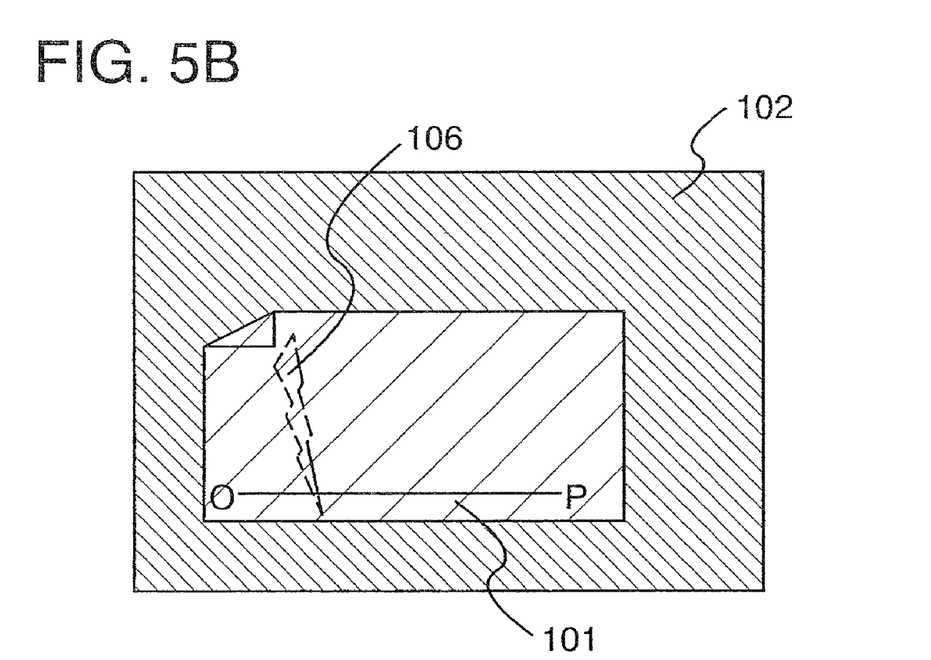

FIGS. 5A and 5B each show a top view of FIG. 2C. FIG. 2C corresponds to a cross-sectional view taken along the line OP in each of FIGS. 5A and 5B. In FIGS. 5A and 5B, the relief layer 103, the separation layer 104, and the substrate 105 are provided below the thin-film stack body 102 as shown in FIG. 2C. The thin-film stack body 102 has the opening portion 106 and the supporting body 101 is attached to cover the opening portion 106. Note that the supporting body 101 is not necessarily formed over the entirely over the thin-film stack body 102 and the opening portion 106, but the supporting body may be attached to cover the entire opening portion 106 as shown in FIG. 5B. It is preferable that the supporting body 101 is attached so as not to cover the entire opening portion 106 and to expose the opposite ends of the opening portion 106 as shown in FIG. 5A. When the supporting body 101 is attached as shown in FIG. 5A, separation can be carried out smoothly.

Figure 2D:
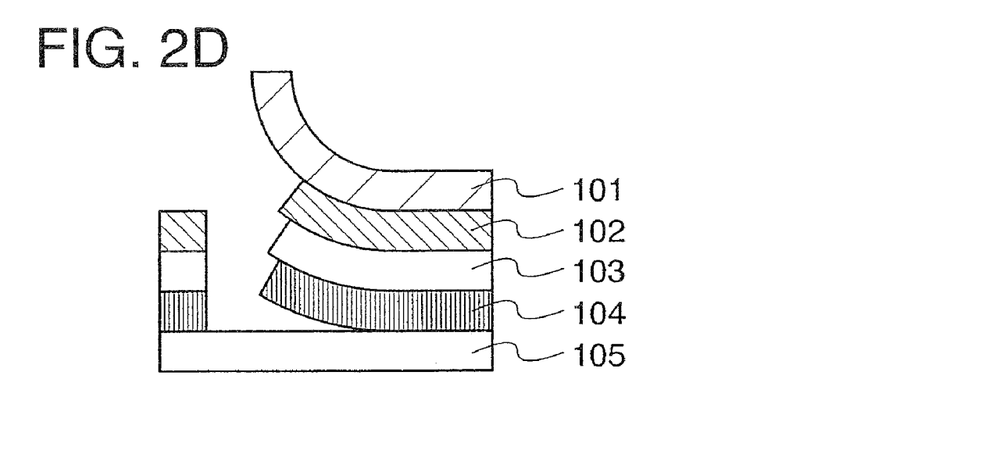

Next, the separation layer 104, the relief layer 103, the thin-film stack body 102, and the supporting body 101 are separated from the substrate 105 (see FIG. 2D). In the foregoing manner, an analytical sample having a stack body including the separation layer 104, the relief layer 103, the thin-film stack body 102, and the supporting body 101, which are separated from the substrate 105, is obtained.

Note that in the separation of the analytical sample from the substrate 105, when the supporting body 101 is peeled off using the preformed opening portion 106 as a start, the separation can be carried out at the interface between the separation layer 104 and the substrate 105 which serves as a boundary without a complicated step. The supporting body 101 after the separation has the separation layer 104, the relief layer 103, and the thin-film stack body, which are transferred to the supporting body 101 from the substrate 105 where they are formed before the separation. Note that since the analytical sample is separated with the separation layer 104 serving as a boundary, the separation layer 104 transferred to the supporting body may be partially thin.

In the foregoing manner, the analytical sample can be manufactured which has a stacked body including the supporting body 101, the thin-film stack body 102, the relief layer 103, and the separation layer 104.

Figure 6:
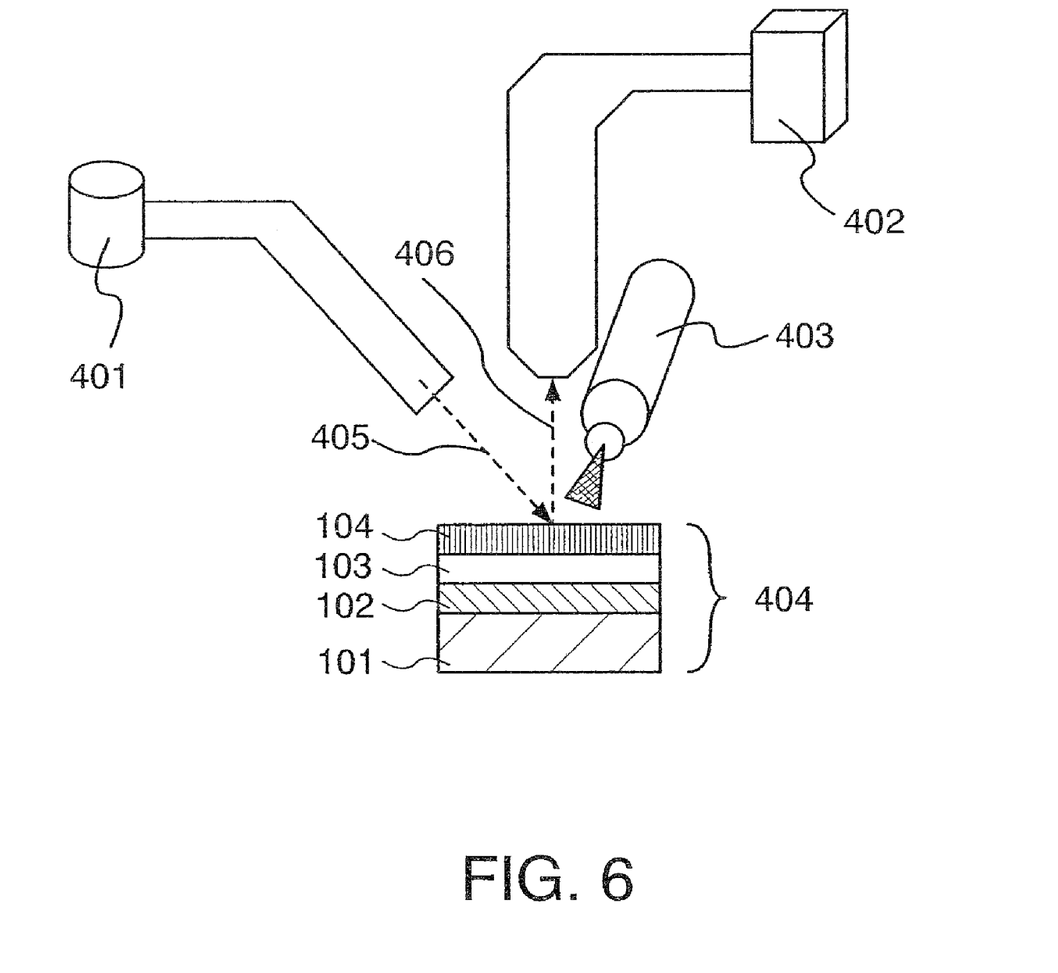
FIG. 6 is a schematic diagram of SIMS of an analytical sample manufactured according to the present invention.

Next, a method of analyzing the analytical sample manufactured according to the present invention is described. FIG. 6 shows a schematic diagram of SIMS. In a schematic diagram showing a state of SIMS, a SIMS apparatus includes an ion source 401, a detector 402, and a neutralization gun 403. A surface of an analytical sample 404 is sputtered with primary ions 405 emitted from the ion source 401, and secondary ions 406 are generated from the surface of the analytical sample. The detector 402 detects the secondary ions 406, so that the analytical sample 404 manufactured according to the present invention can be analyzed.

The ion source has a structure in which cesium ions ($Cs^+$) are generated by heating a tank including solid cesium by a heater. Cesium ions ($Cs^+$) which are the primary ions 405 are electrically accelerated and collide with the analytical sample 404, so that the secondary ions 406 are generated. The secondary ions 406 include a large amount of neutral particles, a small amount of cations, and a small amount of anions. When the secondary ions 406 include elements which are generally called atmospheric components, such as hydrogen, carbon, nitrogen, oxygen, or fluorine, the anions are introduced into the detector 402, and a trace amount of impurities contained in the analytical sample 404 is detected by a quadrupole mass spectrometer in the detector 402.

The neutralization gun 403 is an electron gun to prevent charge build-up (electrification) of the analytical sample 404 due to irradiation with the primary ions 405 and to neutralize the analytical sample electrically. The neutralization gun is used to irradiate a region irradiated with the primary ions 405 in the surface of the analytical sample 404 with charge having opposite polarity with respect to charge of the electrification. The use of the neutralization gun 403 can prevent charge build-up of the analytical sample 404. In addition, in the case in which the analytical sample 404 is directly on an insulating substance, such as a glass substrate or an organic substance (e.g., a tape), generation of charge build-up can be prevented and the secondary ions 406 can be generated stably.

The analytical sample 404 has a stacked layer structure in which the separation layer 104, the relief layer 103, and the thin-film stack body 102 are stacked over the supporting body 101. As shown in FIG. 6, the separation layer 104 is irradiated with the primary ions 405 and sputtered; then, the secondary ions 406 are detected. In other words, in the analytical sample 404, the composition of a film is analyzed sequentially from the separation layer 104. Since the thickness of the separation layer is extremely small compared with that of the substrate, the affect of the crater edge effect and the like is negligibly small.

As described above, according to the present invention, a rear surface of a sample can be emitted with primary ions without polishing a substrate. Therefore, concentration distribution of an impurity can be analyzed highly precisely without complicated steps. In other words, analysis of an impurity in the depth direction can be carried out highly precisely without a step of polishing the substrate.

According to the present invention, in the case in which an impurity is distributed at a high concentration in a surface of the top layer of thin films, for example, when the impurity is added with ion doping by ion injecting apparatus, impurity analysis can be carried out with excellent accuracy from a lower layer of the thin films, which is a region where the impurity is distributed at a low concentration.

Embodiment 1

A result of analysis of concentration distribution in the depth direction by SIMS according to the present invention is described.

Figure 7:
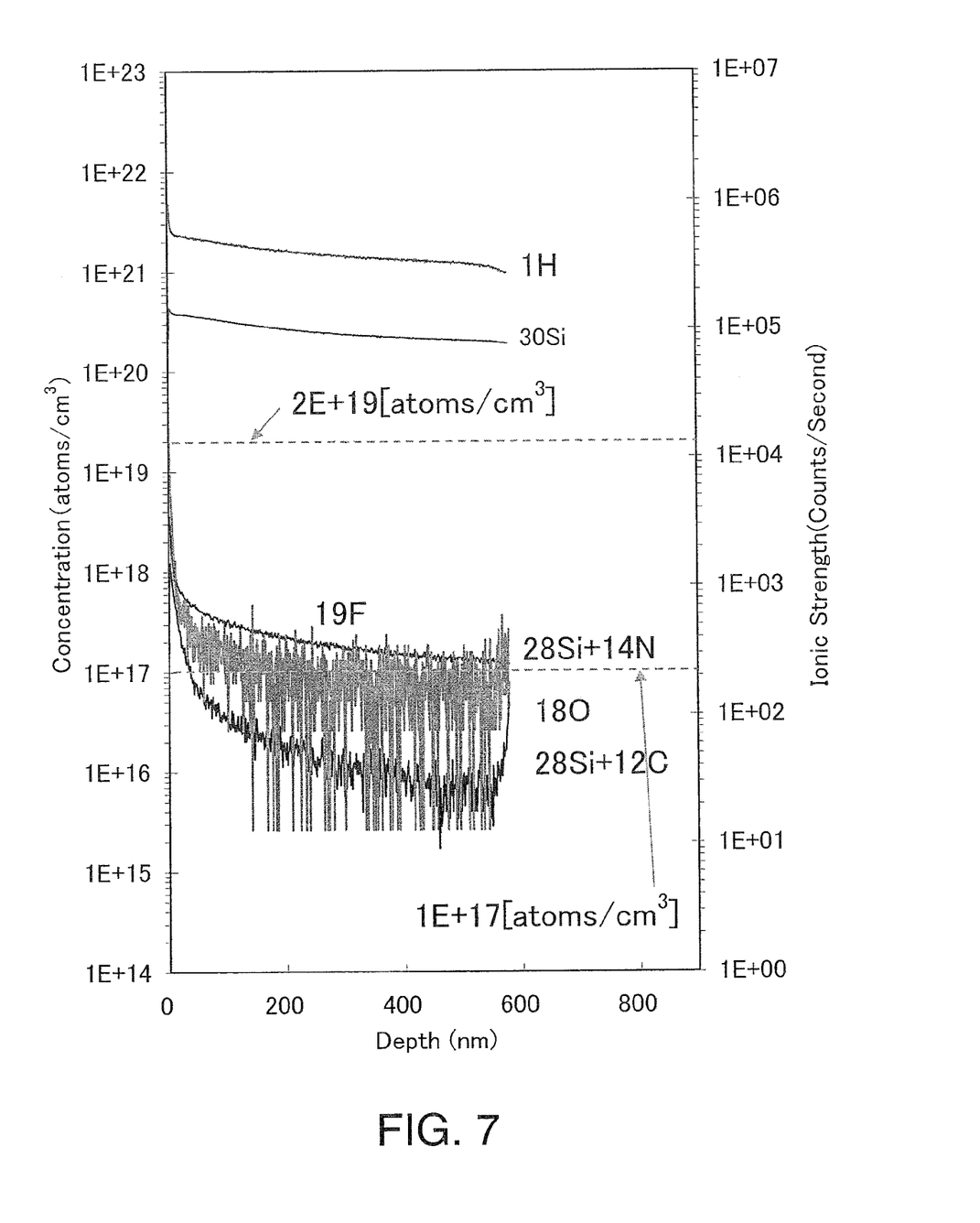
FIG. 7 shows a result of SIMS according to the present invention.

FIG. 7 shows a result of analysis (profile) of a sample A by SIMS, which is manufactured according to the present invention. The sample A has a similar structure to that of the analytical sample 404 described in Embodiment Mode, in which a thin-film stack body to be analyzed, a relief layer, and a separation layer are sequentially stacked over a Kapton (registered trademark) tape used as a supporting body having an adhesive property. In the sample A, the separation layer 104 side is irradiated with primary ions and the sample A is analyzed by SIMS. Note that the sample A is adhered to a stage and firmly fixed so that the sample A is not deformed due to heat generated by a neutralization gun (e.g., electron gun).

In this embodiment, a Kapton (registered trademark) tape refers to a tape in which a Kapton (registered trademark) film is used as a base material and a silicone-based adhesive is used as an adhesive, which is, for example, used as a masking tape in soldering of a printed board.

Figure 8:
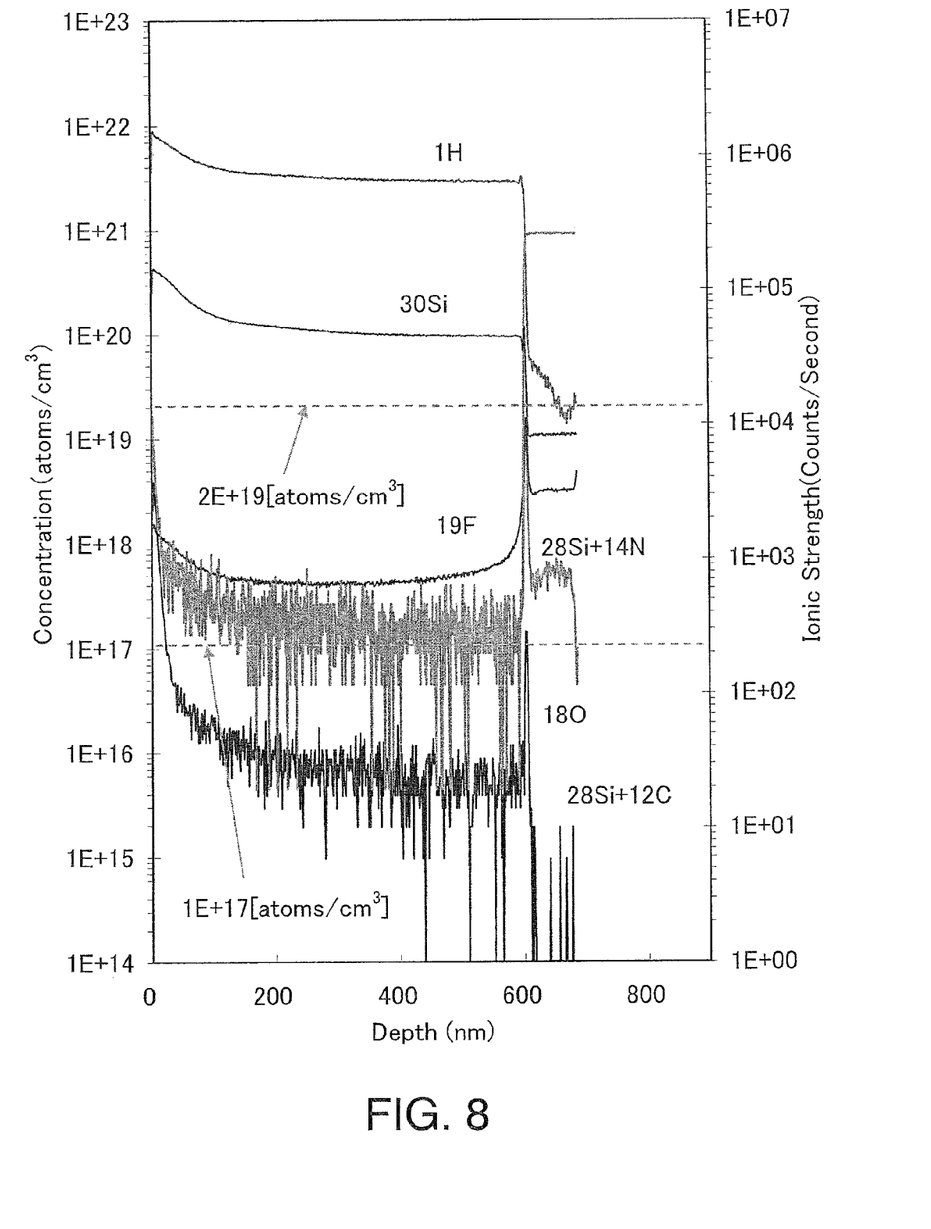
FIG. 8 shows a result of SIMS of a conventional analytical sample.

FIG. 8 shows a result of analysis (profile) of a sample B by SIMS, which is a comparative example. The sample B has a similar structure to the stacked layer structure described in Embodiment Mode, with reference to FIG. 2A in which a separation layer, a relief layer, and a thin-film stack body are stacked in this order over a glass substrate. In the sample B, the thin-film stack body side (a surface side of the top layer) is irradiated with primary ions and the sample B is analyzed by SIMS. Note that the sample A has a structure in which a supporting body having an adhesive property is attached onto the thin-film stack body which is formed through the same steps as those of the sample B, so that the thin-film stack body is transferred. Accordingly, the sample A has the separation layer, the relief layer, and the thin-film stack body which are the same as those of the sample B.

In SIMS of the sample A and the sample B, elements to be measured are silicon, hydrogen, carbon, nitrogen, oxygen, and fluorine. Note that in FIGS. 7 and 8, silicon, hydrogen, carbon, nitrogen, oxygen, and fluorine are denoted by Si, H, C, N, O, and F, respectively. In each of FIGS. 7 and 8, the horizontal axis indicates the depth from an irradiation surface and the vertical axis indicates the ionic strength.

In FIG. 8, the ionic strength of silicon is stable at about $5 \times 10^4$ counts/second.

In FIG. 7, the ionic strength of silicon is stable at about $8 \times 10^4$ counts/second. That is, the ionic strength of silicon in FIG. 7 is stable at almost the same degree as that in FIG. 8.

The comparison between FIGS. 7 and 8 reveals that in the case to which the present invention is applied (the case of carrying out separation shown in FIG. 7), analysis can be carried out similarly to the case to which the present invention is not applied (the case without separation shown in FIG. 8).

Embodiment 2

Concentration distributions in the depth direction are analyzed by SIMS in a sample in which separation is carried out according to the present invention and a sample in which separation is not carried out, and then compared. The result is described below.

Figure 9:
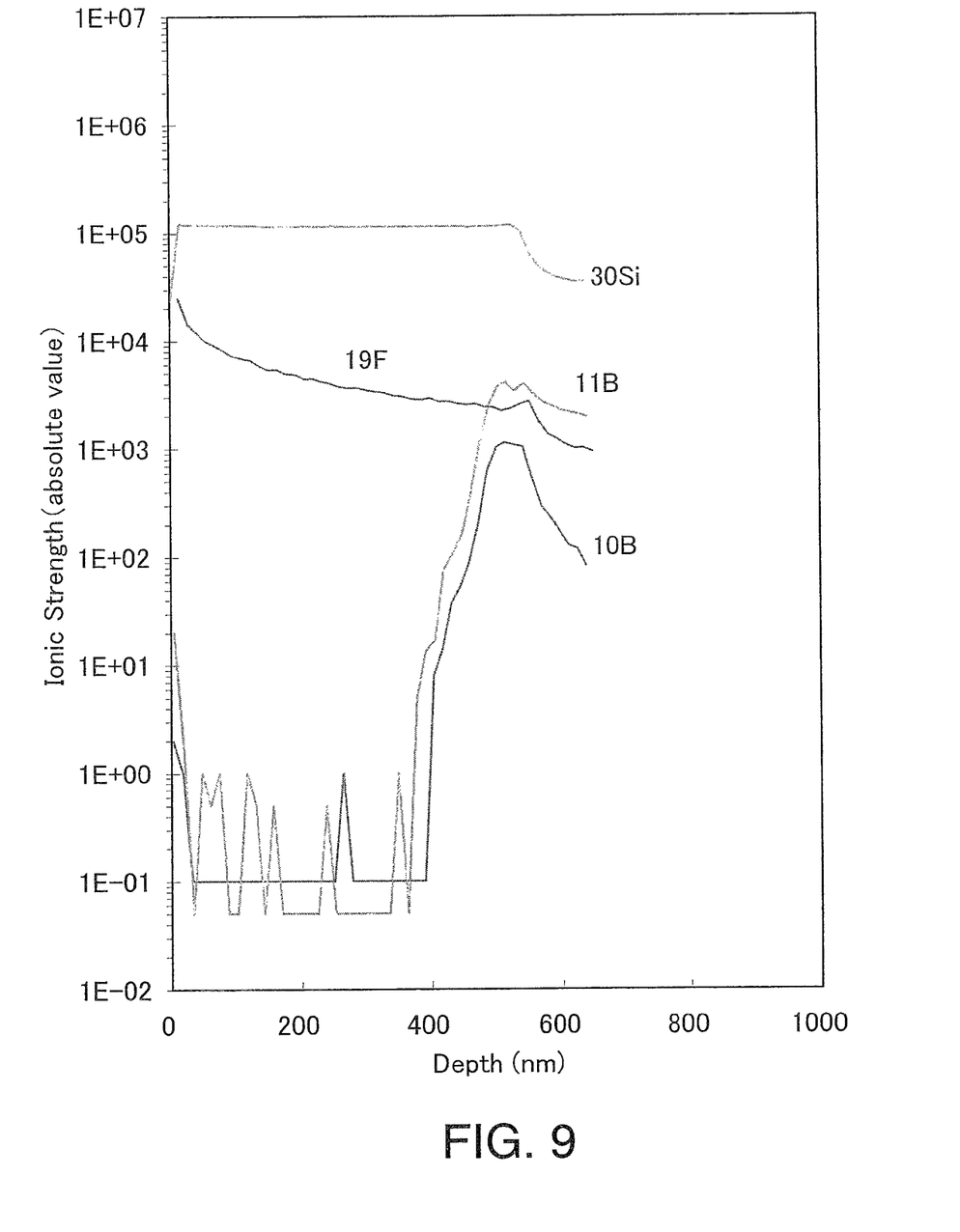
FIG. 9 shows a result of SIMS of an analytical sample manufactured according to the present invention.

An analytical result of a silicon film doped with boron (B) as an impurity element is described. FIG. 9 shows a result of analysis (profile) of a sample C by a SIMS, which is manufactured according to the present invention. The sample C has a similar structure to that of the analytical sample 404 described in Embodiment Mode, in which silicon films formed as a thin-film stack body to be analyzed and a relief layer, and a silicon film containing fluorine formed as a separation layer are stacked in this order over a Kapton (registered trademark) tape which is used as a supporting body having an adhesive property. The silicon films formed as a thin-film stack body to be analyzed and a relief layer are doped with boron (B). In the sample C, the separation layer side is irradiated with cesium (Cs$^+$) as primary ions and the sample C is analyzed by SIMS. Note that the sample C is adhered to a stage and firmly fixed so that the sample C is not deformed due to heat generated by a neutralization gun (electron gun).

In this embodiment, a Kapton (registered trademark) tape refers to a tape in which a Kapton (registered trademark) film is used as a base material and a silicone-based adhesive is used as an adhesive, which is, for example, used as a masking tape in soldering of a printed board.

Figure 10:
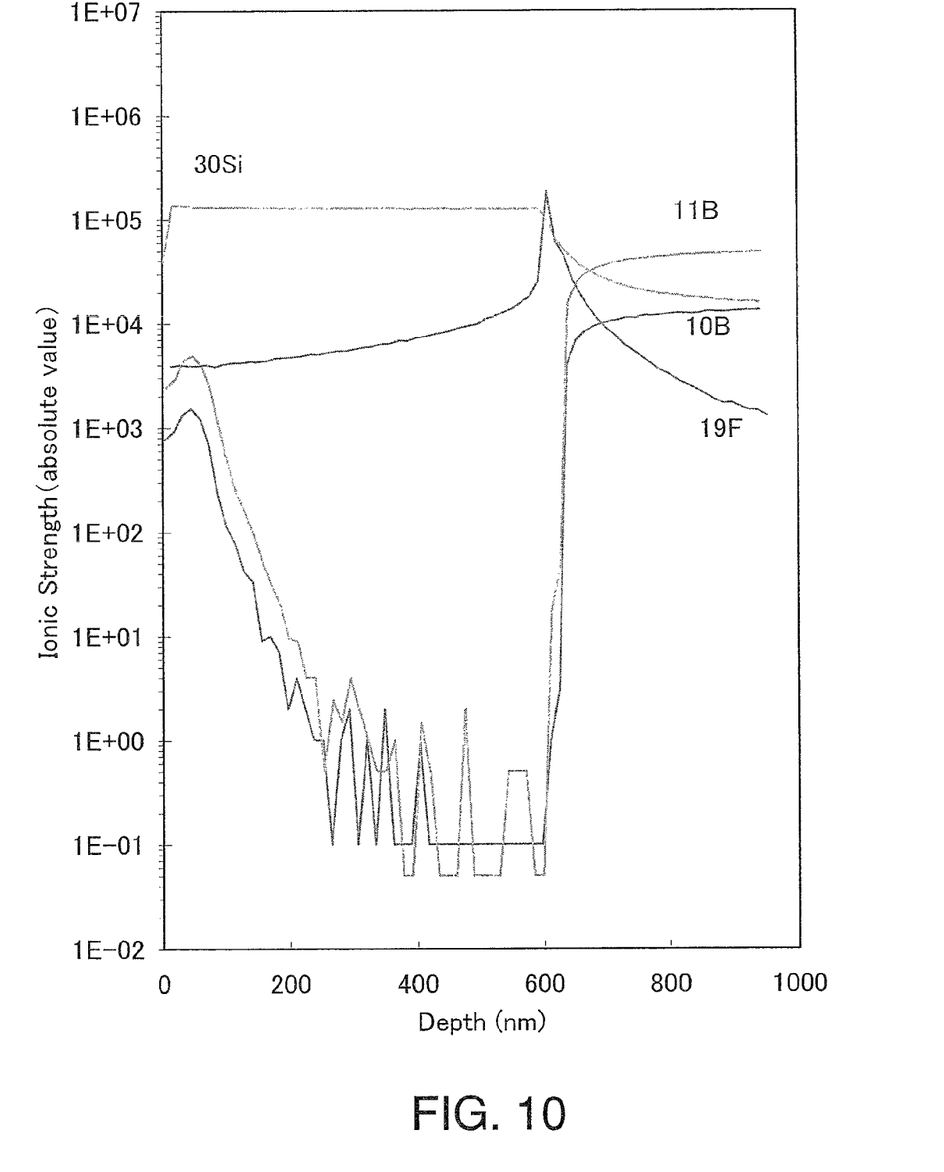
FIG. 10 shows a result of SIMS of a conventional analytical sample.

FIG. 10 shows a result of analysis (profile) of a sample D by SIMS, which is a comparative example. The sample D has a similar structure to the stacked layer structure in FIG. 2A described in Embodiment Mode in which a separation layer, a relief layer, and a thin-film stack body are stacked in this order over a glass substrate. In the sample D, the thin-film stack body side (a surface side of the top layer) is irradiated with cesium (Cs$^+$) as primary ions and the sample D is analyzed by SIMS. Note that the sample C has a structure in which a supporting body having an adhesive property is attached onto the thin-film stack body which is fowled through the same steps as those of the sample B, so that the thin-film stack body is transferred. Accordingly, the sample C has the separation layer, the relief layer, and the thin-film stack body which are the same as those of the sample D. Each of the samples C and D are analyzed with acceleration voltage of 3 kV and current density of 100 nA.

In SIMS of the sample C and the sample D, elements to be measured are boron, silicon, and fluorine. Note that in FIGS. 9 and 10, boron, silicon, and fluorine are denoted by B, Si, and F, respectively. As to boron, both $^{11}$B and $^{10}$B, which is an isotope thereof, are detected. Note that in each of FIGS. 9 and 10, the horizontal axis indicates the depth from an irradiation surface and the vertical axis indicates the ionic strength.

In comparison between FIGS. 9 and 10, ionic strength is gradually changed at the interface between the silicon film and the silicon film doped with boron in FIG. 10, whereas the ionic strength is drastically changed at the interface in FIG. 9, which clearly shows the position of the interface.

Figure 11:
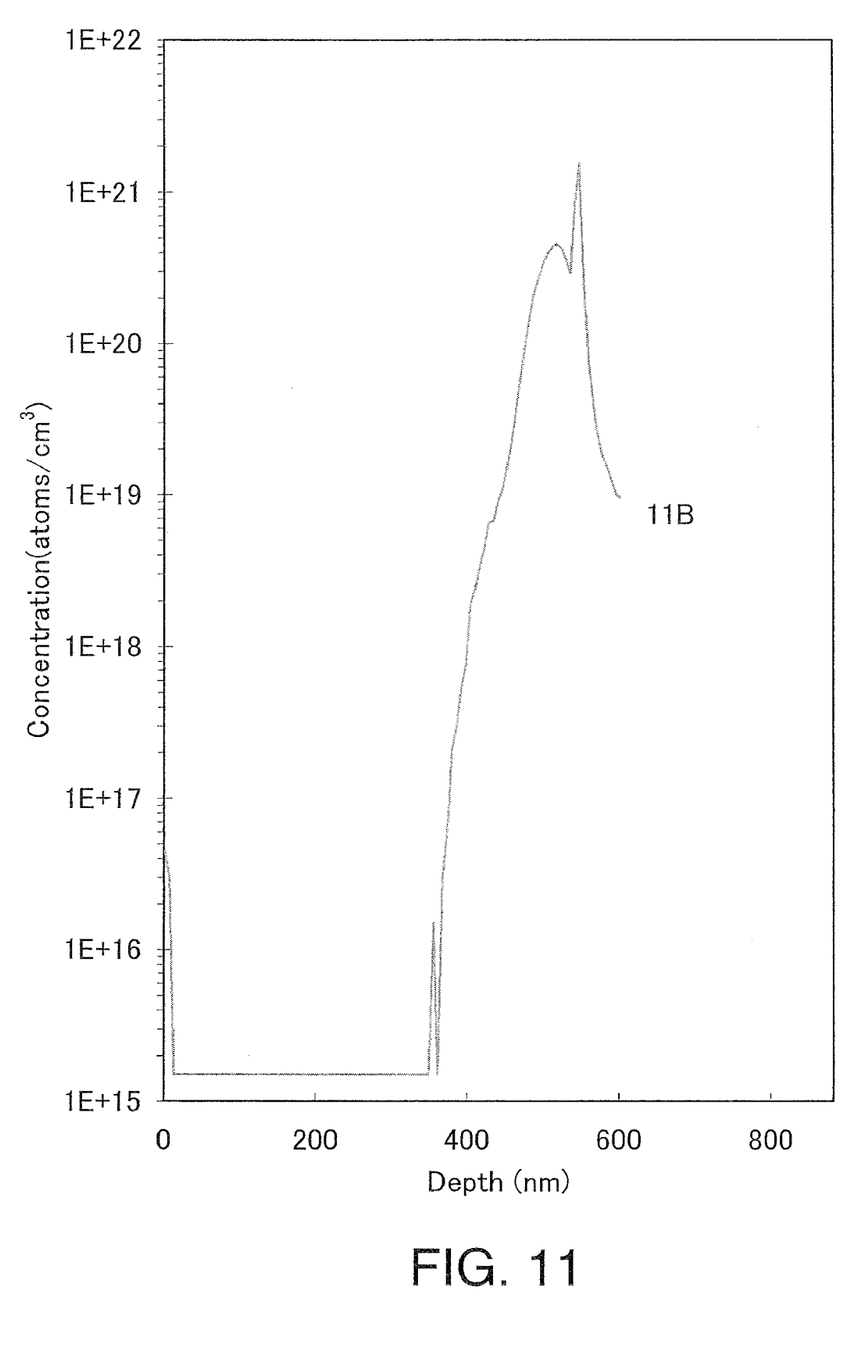
FIG. 11 shows a result of SIMS of an analytical sample manufactured according to the present invention.
Figure 12:
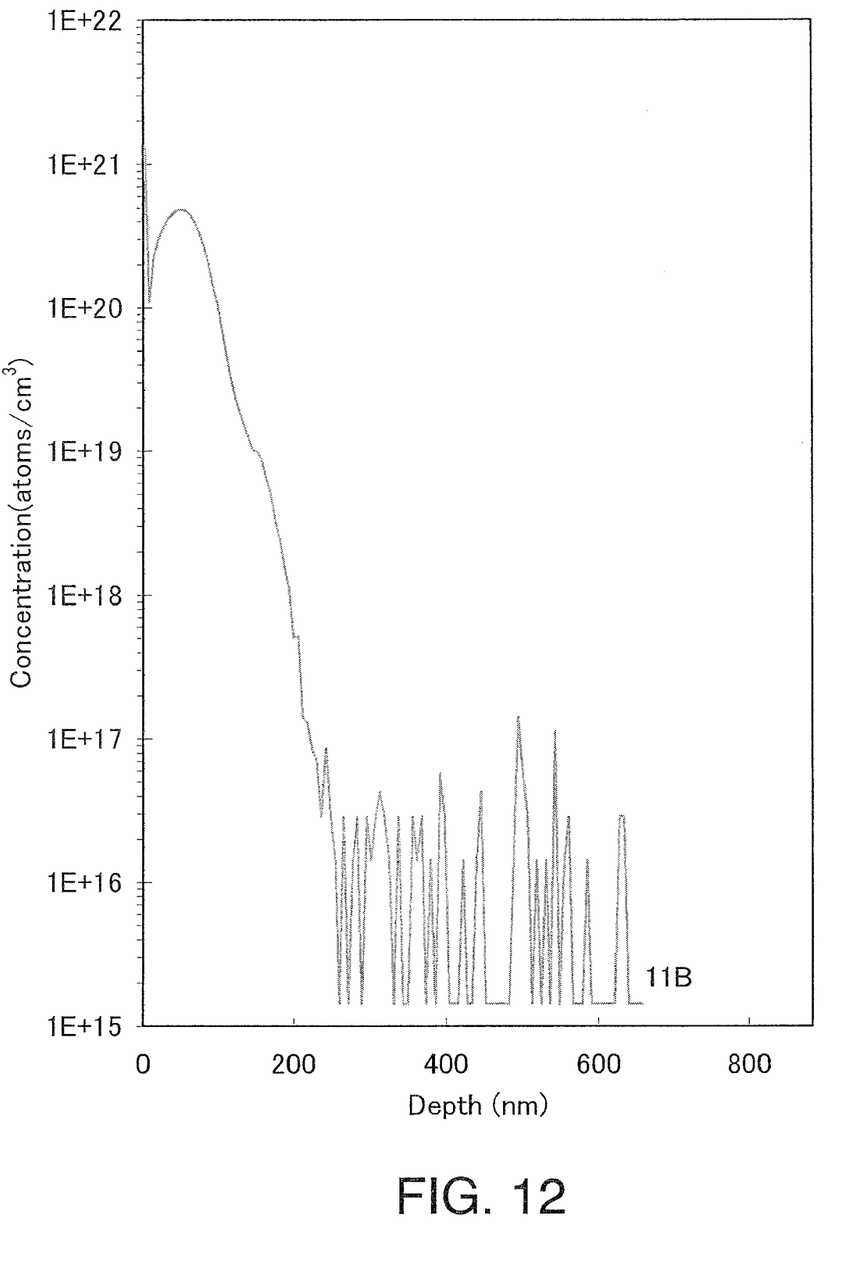
FIG. 12 shows a result of SIMS of a conventional analytical sample.

Further, FIGS. 11 and 12 show results of analyses (profiles) by SIMS of boron (B) in the samples C and D to which $O_2$ is used as primary ions emitted thereto. In FIG. 12, the boron concentration is gradually changed at the interface between the silicon film and the silicon film doped with boron as in FIG. 10. In FIG. 11, the boron concentration is drastically changed at the interface as in FIG. 9, which clearly shows the position of the interface.

In the comparison between FIGS. 9 and 10, and between FIGS. 11 and 12, it is considered that since the sample D is analyzed from the thin-film stack body side, boron elements on the periphery are detected due to the crater edge effect, so that the position of the interface between the silicon film and the silicon film doped with boron becomes unclear. On the other hand, it is also considered that since the sample C to which the present invention is applied is analyzed from the separation layer side, the sample C can be analyzed with excellent accuracy as in a method in which a rear surface of a substrate is polished and the polished surface is irradiated with primary ions for analysis by SIMS; accordingly, the position of the interface between the silicon film and the silicon film doped with boron becomes clear in the data of the analytical result.

As described above, according to the present invention, a SIMS sample can be easily manufactured and the sample can be analyzed highly precisely as in a method in which a rear surface of a substrate is polished and the polished surface is irradiated with primary ions for analysis by SIMS. In other words, the concentration distribution in the depth direction can be analyzed more precisely.

This application is based on Japanese Patent Application serial no. 2006-296745 filed in Japan Patent Office on Oct. 31, 2006, the entire contents of which are hereby incorporated by reference.

What is claimed is:

1. A method of manufacturing an analytical sample by a secondary ion mass spectrometry method, comprising:

forming a separation layer comprising an amorphous silicon film over a glass substrate;

forming a relief layer comprising an amorphous silicon film over a separation layer;

forming one of a thin film and a thin-film stack body to be analyzed over the relief layer;

forming an opening portion in one of the thin film and the thin-film stack body;

attaching a supporting body to one of a surface of the thin film and a surface of a top layer of the thin-film stack body; and peeling off one of the thin film and the thin-film stack body from the glass substrate.

2. The method of manufacturing an analytical sample according to claim 1, wherein the opening portion is formed by a physical means.

3. The method of manufacturing an analytical sample according to claim 1, wherein the supporting body includes a base material and an adhesive over a surface of the base material, and wherein the adhesive contains organopolysiloxane.

4. The method of manufacturing an analytical sample according to claim 1, wherein the separation layer is a film with a hydrogen concentration of $1\times10^{21}$ atoms/cm$^3$ or more and $1\times10^{22}$ atoms/cm$^3$ or less, a carbon concentration of $1\times10^{15}$ atoms/cm$^3$ or more and $2\times10^{18}$ atoms/cm$^3$ or less, a nitrogen concentration of $1\times10^{18}$ atoms/cm$^3$ or more and $1\times10^{20}$ atoms/cm$^3$ or less, and an oxygen concentration of $1\times10^{15}$ atoms/cm$^3$ or more and $1\times10^{19}$ atoms/cm$^3$ or less.

5. The method of manufacturing an analytical sample according to claim 1, wherein the relief layer is a film with a hydrogen concentration of $1\times10^{21}$ atoms/cm$^3$ or more and $1\times10^{22}$ atoms/cm$^3$ or less, a carbon concentration of $1\times10^{15}$ atoms/cm$^3$ or more and $2\times10^{18}$ atoms/cm$^3$ or less, a nitrogen concentration of $1\times10^{18}$ atoms/cm$^3$ or more and $1\times10^{20}$ atoms/cm$^3$ or less, and an oxygen concentration of $1\times10^{15}$ atoms/cm$^3$ or more and $1\times10^{19}$ atoms/cm$^3$ or less.

6. The method of manufacturing an analytical sample according to claim 1, wherein the separation layer and the relief layer are same layer.

7. The method of manufacturing an analytical sample according to claim 1, wherein one of the thin film and the thin-film stack body, the separation layer and the relief layer are same layer.

8. A method of analyzing an analytical sample by a secondary ion mass spectrometry method, comprising:

forming a separation layer comprising an amorphous silicon film over a glass substrate;

forming a relief layer comprising an amorphous silicon film over a separation layer;

forming one of a thin film and a thin-film stack body to be analyzed over the relief layer;

forming an opening portion in one of the thin film and the thin-film stack body to be analyzed;

attaching a supporting body to one of a surface of the thin film and a surface of a top layer of the thin-film stack body;

peeling off one of the thin film and the thin-film stack body from the glass substrate; and irradiating a surface of the separation layer with primary ions to analyze one of the thin film and the thin-film stack body.

9. The method of analyzing an analytical sample according to claim 8, wherein the separation layer is an amorphous silicon film.

10. The method of analyzing an analytical sample according to claim 8, wherein the opening portion is formed by a physical means.

11. The method of analyzing an analytical sample according to claim 8, wherein the supporting body includes a base material and an adhesive over a surface of the base material, and wherein the adhesive contains organopolysiloxane.

12. The method of analyzing an analytical sample according to claim 8, wherein the separation layer is a film with a hydrogen concentration of $1\times10^{21}$ atoms/cm$^3$ or more and $1\times10^{22}$ atoms/cm$^3$ or less, a carbon concentration of $1\times10^{15}$ atoms/cm$^3$ or more and $2\times10^{18}$ atoms/cm$^3$ or less, a nitrogen concentration of $1\times10^{18}$ atoms/cm$^3$ or more and $1\times10^{20}$ atoms/cm$^3$ or less, and an oxygen concentration of $1\times10^{15}$ atoms/cm$^3$ or more and $1\times10^{19}$ atoms/cm$^3$ or less.

13. The method of analyzing an analytical sample according to claim 8, wherein the relief layer is a film with a hydrogen concentration of $1\times10^{21}$ atoms/cm$^3$ or more and $1\times10^{22}$ atoms/cm$^3$ or less, a carbon concentration of $1\times10^{15}$ atoms/cm$^3$ or more and $2\times10^{18}$ atoms/cm$^3$ or less, a nitrogen concentration of $1\times10^{18}$ atoms/cm$^3$ or more and $1\times10^{20}$ atoms/cm$^3$ or less, and an oxygen concentration of $1\times10^{15}$ atoms/cm$^3$ or more and $1\times10^{19}$ atoms/cm$^3$ or less.

14. The method of manufacturing an analytical sample according to claim 8, wherein the separation layer and the relief layer are same layer.

15. The method of manufacturing an analytical sample according to claim 8, wherein one of the thin film and the thin-film stack body, the separation layer and the relief layer are same layer.

* * * * *